(12) United States Patent
Juillerat

(10) Patent No.: US 9,717,506 B2
(45) Date of Patent: Aug. 1, 2017

(54) HAND PIECE FOR DENTAL OR SURGICAL APPLICATIONS

(71) Applicant: BIEN-AIR HOLDING SA, Bienne (CH)

(72) Inventor: Sébastien Juillerat, Moutier (CH)

(73) Assignee: Bien-Air Holding SA, Bienne (CH)

( * ) Notice: Subject to any disclaimer, the term of this patent is extended or adjusted under 35 U.S.C. 154(b) by 0 days.

(21) Appl. No.: 14/748,462

(22) Filed: Jun. 24, 2015

(65) Prior Publication Data

US 2015/0374385 A1 Dec. 31, 2015

(30) Foreign Application Priority Data

Jun. 27, 2014 (EP) ..................................... 14174754

(51) Int. Cl.
*A61C 3/00* (2006.01)
*A61B 17/16* (2006.01)
*A61C 1/14* (2006.01)

(52) U.S. Cl.
CPC ............ *A61B 17/162* (2013.01); *A61C 1/141* (2013.01); *A61C 1/144* (2013.01); *A61B 17/1673* (2013.01)

(58) Field of Classification Search
CPC ... A61B 17/162; A61B 17/1673; A61C 1/141; A61C 1/144
USPC .......................... 433/127, 128, 129, 126, 114
See application file for complete search history.

(56) References Cited

U.S. PATENT DOCUMENTS 4,773,856 A * 9/1988 Mosimann .............. A61C 1/141
433/127
5,518,398 A * 5/1996 Nakanishi .............. A61C 1/141
433/127

* cited by examiner

*Primary Examiner* — Michael Carey
(74) *Attorney, Agent, or Firm* — Notaro, Michalos & Zaccaria P.C.

(57) ABSTRACT

A handpiece for dental or surgical applications has a chuck for rotatably clamping a tool such as a bur, the chuck being drivingly connectable to a drive mechanism such as to rotate the tool about a rotation axis thereof, a push button operatively connected to the chuck, configured to release the tool from the chuck upon depressing the push button, a spherical element, preferably a ball, fitted within or mounted at the push button, arranged and configured such that, when the push button is depressed, the spherical element enters into contact with the chuck, the spherical element being of a material with a high hardness on the Vickers scale of >2000.

9 Claims, 4 Drawing Sheets

HAND PIECE FOR DENTAL OR SURGICAL APPLICATIONS

FIELD OF THE INVENTION

The present invention relates to handpieces, in particular handpieces for dental or surgical applications.

BACKGROUND OF THE INVENTION

Handpieces for dental or surgical applications are used for a multitude of clinical procedures. Carrying out these procedures is done with a large selection of burs. Changing the burs during a procedure or in between procedures is done through a mechanism in the head of the handpiece which is activated by a push button. To release/introduce a bur, the push button is depressed (pressed down) to activate a release mechanism of the chuck. During a procedure, in particular a dental procedure, the handpiece is introduced in the oral cavity, for example to remove caries. To access a tooth from the vestibular side, the soft tissue (cheek) must be pushed away, in order to create the space necessary for the handpiece and the bur. If this is done using the handpiece itself, there is a risk that the push button is depressed during the procedure while the bur is rotating, thus creating friction between the rotating part of the chuck and the non-rotating push button. With a rotation speed in the range between 40,000 and 400,000 rpm, heat builds up very quickly with the risk of burns to the soft tissue.

The published patent application FR2679804A1 of the applicant related to a handpiece describes an early approach to solve the problem of overheating of the push button by means of stainless steel bearing ball mounted on the rotating part of the chuck. The push button enters in contact with the ball when being depressed. The small contact surface (theoretically a single point) between bearing ball and push button limits the build-up of heat in the push button even if the chuck is rotating. In order to limit wear-out of the push button, a small washer of hard-metal has been soldered to the inner side of the push button, delaying heat build-up. Nevertheless, the friction will end up generating heat in the hard metal washer which transmits the heat directly to the push button and potentially to the patient. Finally, the stainless steel ball will wear out with time, increasing the contact surface with the push button.

Several alternative approaches have been developed to overcome the problem such as:
- integrating a ball bearing in the Push-Button and using the inner and outer ring of the ball bearing to insulate the push-button from heat-transmission. However, in addition to being an expensive solution, the ball bearing is used in a way that leads to fast wear-out of the ball bearing;
- Providing the chuck mechanism with a rounded end in hard metal. However, due to the large geometry, the heat protection of this design is very limited.

Technical Problem to be Solved

The objective of the present invention is therefore to provide a handpiece for dental or surgical applications having a chuck and a push button operatively connected to releasably hold a tool such as a bur which overcomes the problem of overheating of the push button.

A further objective of the present invention is to ensure that wear-out of the parts providing the overheating protection is significantly reduced thereby prolonging the lifetime of the handpiece.

SUMMARY OF THE INVENTION

The above-identified objectives of the present invention are solved by a handpiece for dental or surgical applications, comprising a chuck for rotatably clamping a tool such as a bur, the chuck being drivingly connectable to a drive mechanism such as to rotate said tool about a rotation axis thereof. A push button is operatively connected to the chuck, configured to release said tool from the chuck upon depressing the push button. The handpiece is characterized in that a spherical element, preferably a ball, is fitted within the push button, arranged and configured such that—when the push button is depressed—the spherical element enters into contact with the chuck. The spherical element comprises a material with a high hardness on the Vickers scale of >2000 (i.e. HV>2000). Preferred embodiments comprise a material with a high hardness on the Vickers scale of >2300 (i.e. HV>20,300).

The material of the spherical element is chosen so that this element is able to serve as a heat insulating element.

Experiments have been carried out to select a material or group of materials which on the one hand have the properties of a heat insulating element and on the other hand which a highly wear resistant. The wear resistance is crucial since any wear of the spherical element will lead to an increased contact zone or thermal bridge between the push button and the chuck.

Advantageous Effects

The most important advantage of the present invention is that by providing efficient heat insulation between the rotating part of the chuck and the push button, injuries due to overheating of the push button upon accidental depression or misuse thereof can be avoided. A further advantage of the present invention over the known solutions, is that the wear of the heat insulating elements is substantially reduced thereby prolonging the lifetime of not only the push button, but the entire handpiece.

BRIEF DESCRIPTION OF THE DRAWINGS

Further characteristics and advantages of the invention will in the following be described in detail by means of the description and by making reference to the drawings.

Note: The figures are not drawn to scale, are provided as illustration only and serve only for better understanding but not for defining the scope of the invention. No limitations of any features of the invention should be inferred from these figures.

DESCRIPTION OF PREFERRED EMBODIMENTS

Certain terms will be used in this patent application, the formulation of which should not be interpreted to be limited by the specific term chosen, but as to relate to the general concept behind the specific term.

Following, the invention shall be described with reference to the illustrating figures.

Figure 1:
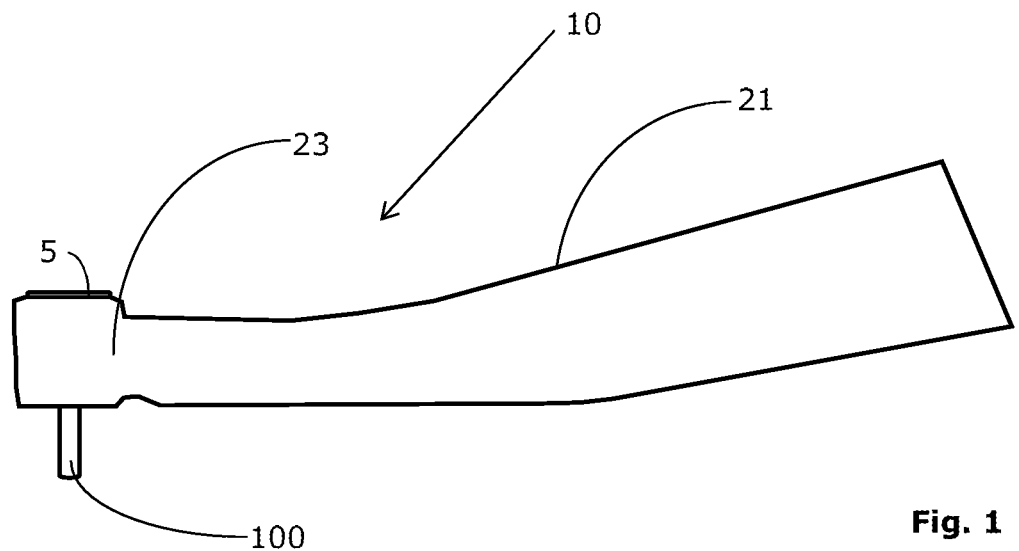
FIG. 1 shows a side view of a handpiece for dental or surgical applications and its various main sections, the handpiece being fitted with a drilling bur.

FIG. 1 shows a side view of a handpiece 10 for dental or surgical applications identifying its main sections, namely the grip section 21 and the head section 23. The handpiece is configured to receive a tool 100, such as a drilling bur.

Figure 2:
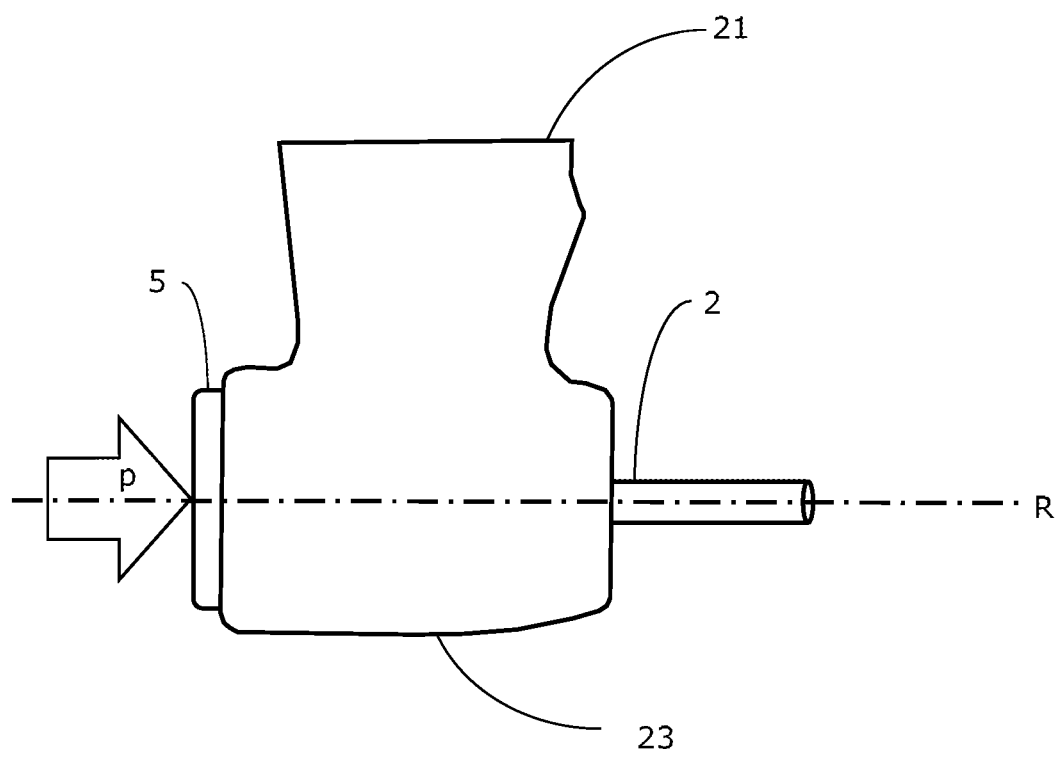
FIG. 2 shows a side view of a handpiece for dental or surgical applications, namely its head section.

Further details of the head section 23 of the handpiece 10 are shown on the exploded partial side view of FIG. 2. As depicted, the head section 23 receives the chuck 2 (only an extension thereof being visible on FIG. 2) and a push button 5, the chuck 2 being arranged to rotate about the rotation axis R together with the tool 100 it is configured to receive.

In accordance with the present invention, a so-called 3D spherical element is employed. Preferably, a ball 7 is used a spherical element for all embodiments.

The spherical element of the invention comprises an enclosing surface which is convex shaped. Preferably, the spherical element of all embodiments is rotationally symmetric.

Well suited are spherical elements which have an oval shape. Very well suited are spherical elements which have a perfect or near perfect ball shape. In the following, reference is made to embodiments which have a ball 7 serving as spherical element.

Figure 4:
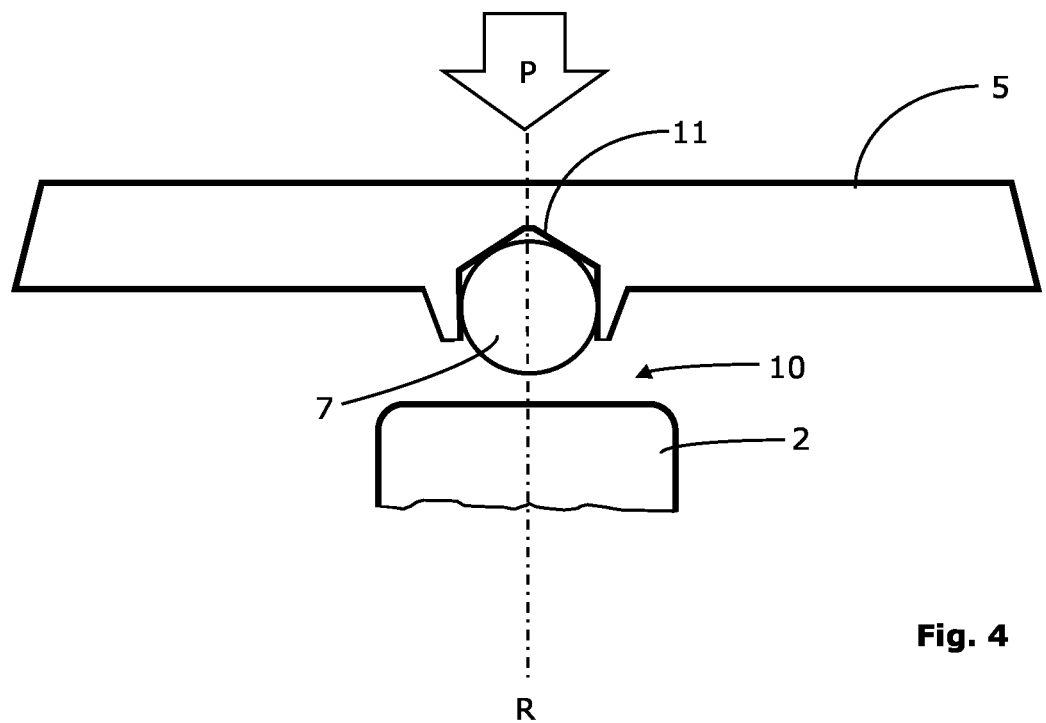
FIG. 4 shows a magnified schematic view of the head section of a further embodiment of the handpiece according to the present invention.
Figure 5:
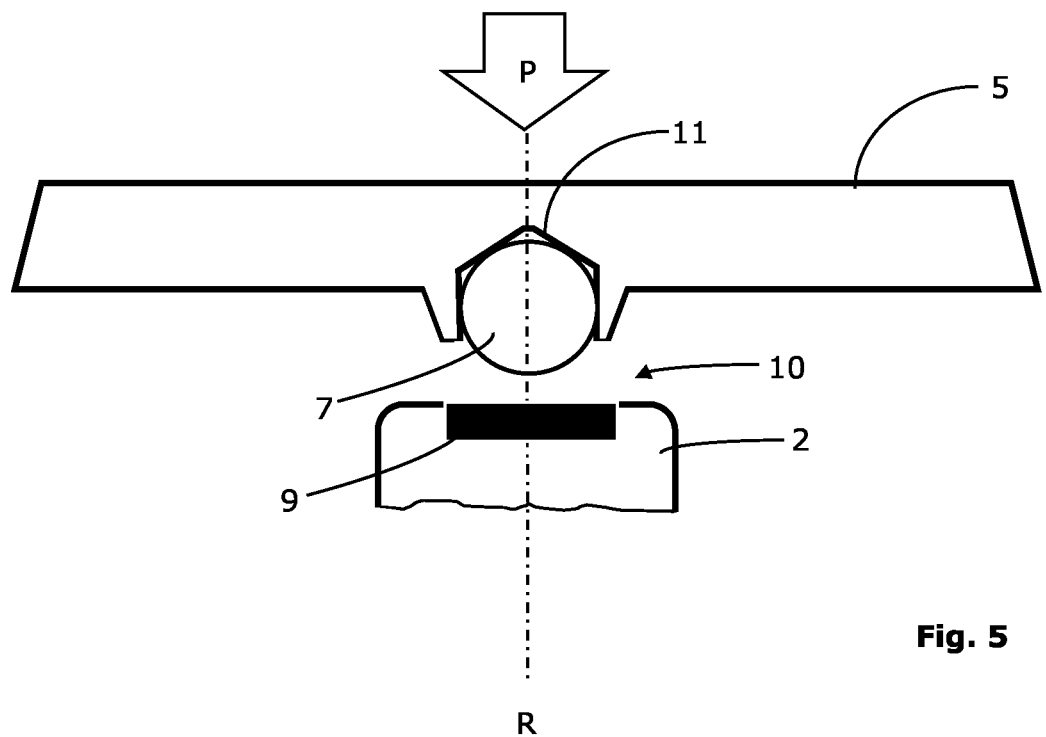
FIG. 5 shows a magnified schematic view of the head section of a further embodiment of the handpiece according to the present invention.

The spherical element, preferably a ball 7, is mounted or placed inside the push button 5 so that, in an assembled state, the handpiece 10 comprises (from top to bottom) the push button 5, followed by the spherical element which in turn is followed by a small air gap 10 and the chuck 2 (cf. FIG. 4 or 5). If the push button 5 is pressed down, the spherical element is caused to contact the chuck 2. In this state, the air gap 10 is not present anymore.

Figure 3:
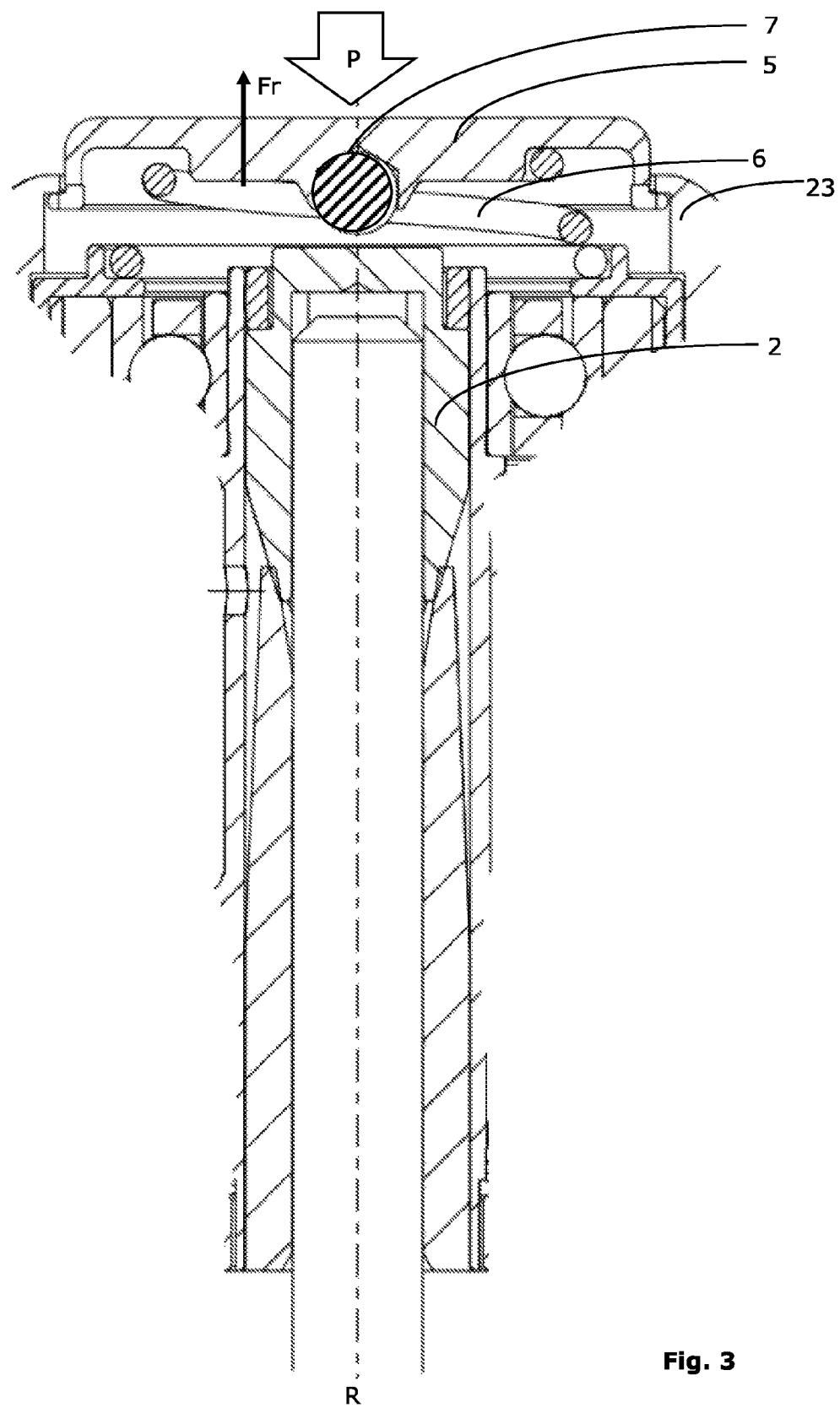
FIG. 3 shows a magnified cross section of the head section of a handpiece for dental or surgical applications according to the present invention.

Preferably, the push button 5 of all embodiments has the shape of a disk or plate with a dome-shaped or convex upper part and a concave lower part, as schematically depicted in FIGS. 4 and 5. In FIG. 3, the convex upper part is pointing upwards and the concave lower part is facing the chuck 2. The spherical element of all embodiments sits at the concave lower side of the push button 5.

In order to ensure a minimum contact between the spherical element and the push button 5, the push button 5 comprises a bay or receiving section having a polygonal cross-section 11, as depicted in FIGS. 4 and 5. These figures are schematic figures only and the various elements are not drawn to scale. As can be derived from FIGS. 4 and 5, the bay or receiving section is in a central position. It preferably has flat non-curved surfaces in a polygonal arrangement so that a minimum number of contact points is provided between the spherical element and the push button 5. The polygonal arrangement might have a pyramid or trapezoid shape in the cross-section. The smaller the contact between the spherical element and the push button 5 is, the less heat is being transferred from the spherical element into the button 5.

In addition, experiments revealed that it is important to choose a material for the spherical element which on the one hand is a good thermal isolator and on the other hand which is as hard as possible since any wear will lead to an increased surface contact between the spherical element and the chuck 2.

In accordance with the invention, the spherical element preferably comprises a material with a high hardness on the Vickers scale of >2000.

Very well suited are ceramic materials. Preferred embodiments thus comprise a ceramic spherical element, preferably a ceramic ball 7.

Experiments in various constellations and arrangements have been carried out in order to find the most well suited materials. These experiments revealed that not all ceramic materials are suitable.

Figure 6:
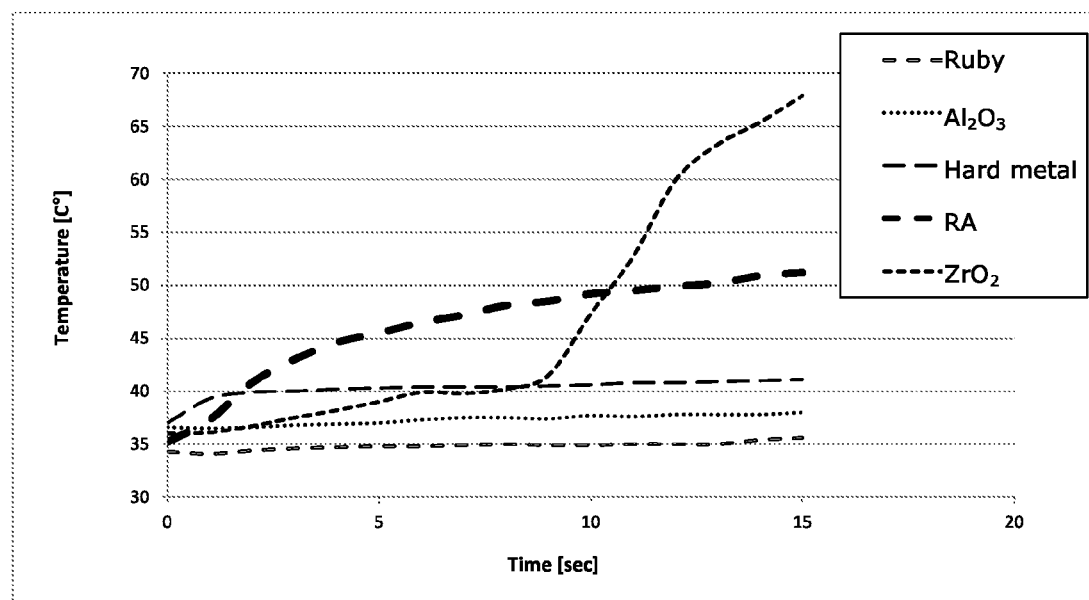
FIG. 6 shows the plotted results of a series of experiments which have been carried out.

FIG. 6 shows the plotted results of a series of experiments which have been carried out. Ruby, Aluminum oxide ($Al_2O_3$), hard metal, RA (a reference design) and Zirconium dioxide ($ZrO_2$) have been tested as possible materials or designs for the spherical element. The diagram reveals that Zirconium dioxide ($ZrO_2$) is not so well suited. Due to fast wear-out of the material, the contact surface of the spherical element increases and heat-up takes place.

The material of the spherical element of all embodiments is preferably selected from the group comprising: natural and synthetic Ruby, Aluminum oxide ($Al_2O_3$), (mineral) corundum, natural and industrial diamond, carbide metal (e.g. Beryllium carbide), hard metal (e.g. Titanium-Carbide Tantalum-Carbide or Tungsten-Carbide), saphir, Silicon Nitride ($Si_3N_4$).

Even better suited are tailored materials which can be based on any of the materials of the above-mentioned group. An example of a tailored material is Aluminum oxide ($Al_2O_3$) with a passivated or hardened surface. The hard metal can be tailored by applying a coating (e.g. TiN (titanium nitride), TiC (titanium carbide)).

If an Aluminum oxide is used, this material is selected and treated so that it has a high hardness on the Vickers scale of >2000 and preferably of >2500. Rubies have a hardness on the Vickers scale of about 2400. Hard metal is selected and treated so that it has a high hardness on the Vickers scale of >2000.

FIG. 3 shows a magnified cross section of a head section 23 of the handpiece 10 according to the present invention, depicting the particulars of the heat-bridge-limiting solution for operatively connecting the push-button 5 with the chuck 2 when the former is depressed (illustrated with a block arrow P).

FIG. 4 is a magnified and schematic partial view of the head section of a further embodiment of the handpiece according to the present invention. This embodiment comprises a chuck 2 which is separated (in the non-depressed state) from the spherical element by an air gap 10.

FIG. 5 is a magnified and schematic partial view of the head section of yet a further embodiment of the handpiece according to the present invention. This embodiment comprises a chuck 2 which is provided with a washer or insert 9 for contacting the ball 7 in order to further reduce wear on the part of the chuck 2 contacting the ball 7. Preferably, the washer or insert of all embodiments is made of hard metal or ceramic material.

Preferably, the handpiece 10 of all embodiments comprises a resilient member 6, such as a coil spring, being arranged such as to provide a return force Fr to force (cf. FIG. 3) the push button 5 into a resting position after being depressed.

Preferably, the handpiece 10 of all embodiments comprises a push button 5 comprising a heat insulating material, preventing heat build-up from being transmitted from the spherical element to an outer surface of the push button 5.

It will be understood that many variations could be adopted based on the specific structure hereinbefore described without departing from the scope of the invention as defined in the following claims.

REFERENCE LIST handpiece 10
grip section 21
head section 23
chuck 2
rotation axis R
reference design RA
push button 5
resilient member 6
spherical element, ball 7
washer, insert 9
air gap 10
polygonal cross-section 11
tool 100

The invention claimed is:

1. A handpiece (10) for dental or surgical applications, comprising:
   a chuck (2) for rotatably clamping a tool (100), the chuck (2) being drivingly connectable to a drive mechanism such as to rotate said tool (100) about a rotation axis (R) thereof;
   a push button (5) operatively connected to said chuck (2), configured to release said tool (100) from the chuck (2) upon depressing the push button (5);
   wherein:
   a spherical element (7), is fitted or mounted within a concave lower part of the push button (5), whereby contact is ensured between the spherical element (7) and the push button (5), said spherical element being arranged and configured such that when the push button (5) is depressed, the spherical element (7) enters into contact with the chuck (2), said spherical element comprising a material with a high hardness on the Vickers scale of >2000.

2. A handpiece (10) according to claim 1, wherein the spherical element is seated in a bay or receiving section of the push button (5) having a polygonal cross-section (11) to reduce thermal bridging between the chuck (2) and the push button (5).

3. A handpiece (10) according to claim 1, wherein the spherical element is made of a material selected from the group: Ruby, Aluminum oxide ($Al_2O_3$), corundum, diamond, carbide metal, hard metal, saphir, $Si_3N_4$.

4. A handpiece (10) according to claim 1, wherein that the chuck (2) is provided with a washer or insert (9) for contacting the spherical element.

5. A handpiece (10) according to claim 4, wherein the washer or insert is made of hard metal to limit the wear-out due to friction between the washer (9) and the spherical element.

6. A handpiece (10) according to claim 1, wherein the handpiece (10) comprises a grip section (21) and a head section (23), the tool (100) protruding from said head section (23) while said push button (5) being arranged at an end of the head section (23) essentially opposite said tool (100).

7. A handpiece (10) according to claim 1, wherein a resilient member (6), such as a coil spring, is arranged such as to provide a return force (Fr) to force the push button (5) into a resting position after being depressed.

8. A handpiece (10) according to claim 1, wherein the push button (5) comprises a heat insulating material, preventing heat build-up from being transmitted from the spherical element to an outer surface of the push button (5).

9. A handpiece (10) according to claim 1, wherein the spherical element is made of a material of thermal conductivity which does not exceed the thermal conductivity of material selected from the group: Ruby, Aluminum oxide ($Al_2O_3$), corundum, diamond, carbide metal, saphir, $Si_3N_4$.

* * * * *